(12) United States Patent
Gagnon

(10) Patent No.: US 6,278,122 B1
(45) Date of Patent: Aug. 21, 2001

(54) KEYBOARD AND MOUSE STERILIZING DEVICE

(76) Inventor: Joseph Ernest Patrick Gagnon, 1518 Englecrest Dr., Richardson, TX (US) 75081

( * ) Notice: Subject to any disclaimer, the term of this patent is extended or adjusted under 35 U.S.C. 154(b) by 0 days.

(21) Appl. No.: 09/255,354

(22) Filed: Feb. 23, 1999

(51) Int. Cl.$^7$ ....................................................... A61L 2/10
(52) U.S. Cl. ......................................... 250/455.11; 422/24
(58) Field of Search ........................... 422/24; 250/492.1, 250/504 R, 455.11

(56) References Cited

U.S. PATENT DOCUMENTS

| | | | |
|---|---|---|---|
| 4,952,812 | * | 8/1990 | Miripol et al. ...................... 422/24 X |
| 4,975,587 | * | 12/1990 | Min-Jenn ............................ 422/24 X |
| 5,225,172 | * | 7/1993 | Meyler et al. ...................... 422/24 X |

* cited by examiner

Primary Examiner—Elizabeth McKane
(74) Attorney, Agent, or Firm—Morgan L. Crow, P.E.

(57) ABSTRACT

A computer keyboard and mouse sterilizing system which has a cabinet and extendable base for storage and support of the keyboard and mouse, and that utilizes an ultra-violet light source for the destruction of microorganisms when the keyboard is not in use.

3 Claims, 2 Drawing Sheets

KEYBOARD AND MOUSE STERILIZING DEVICE

CROSS-REFERENCE TO RELATED APPLICATION

Not Applicable

BACKGROUND OF THE INVENTION

1. Technical Field

This invention relates generally to a sterilizing system and more particularly to an improved and novel sterilizing system for computer keyboards, keypads and computer mice.

2. Description of Related Art

Computer keyboards are subject to constant and repeated touch by the fingertips of users. By the nature of their use, keyboards, keypads, and computer mice accumulate substantial quantities of bacteria and germs. Currently, users will spray disinfectant onto a disposable paper product and then, with the computer turned off, wipe off the keys and the mouse. This method subjects the electronics of the keyboard or keypad and mouse to the liquid spray and risks electrical damage. Liquid disinfecting sprays are also limited in their ability to access all component surfaces which may be infected. Liquid disinfecting sprays are also limited in their ability to kill the various microorganisms that accumulate on the components. Liquid disinfectants are also a nuisance to use, requiring labor and materials, and as a result, they are infrequently used. The use of liquid disinfecting sprays also generates solid waste for disposal.

BRIEF SUMMARY OF THE INVENTION

A primary advantage of the present invention is that it sterilizes computer keyboards, computer mice, and keypads and more effectively kills the various microorganisms that accumulate on these components than previous methods of disinfecting. Another advantage of the present invention is that it automatically sterilizes computer keyboards, computer mice, and keypads without the requirement of manual labor or generation of solid waste. Another advantage of the present invention is that it sterilizes computer keyboards, computer mice, and keypads without the requirement of chemicals, or liquids that might interfere with the electronics. Other advantages of the present invention will become apparent from the following descriptions, taken in connection with the accompanying drawings, wherein, by way of illustration and example, an embodiment of the present invention is disclosed.

In the preferred embodiment of the present invention, a computer keyboard and mouse are located on a retractable base section, which is connected to and supported by an enclosure. A front door is hinge connected to the base. The front door may be opened to provide an armrest for the keyboard operator. The base section may be retracted into the enclosure for storage and sterilization. An ultraviolet light source is located inside of the enclosure. A highly reflective material lines the inside of the enclosure surface. When the base section is in the retracted position, the ultraviolet light may be activated. A position switch can automate activation of the Ultraviolet light. A timer can be used to control the duration of the activation of the Ultraviolet light. A safety interlock switch prevents exposure of the operator to ultraviolet radiation. Operation of the Ultraviolet light effectively destroys the microorganisms that have accumulated on the computer keyboard and mouse.

BRIEF DESCRIPTION OF THE SEVERAL VIEWS OF THE DRAWING(S)

DETAILED DESCRIPTION OF THE INVENTION

Figure 1:
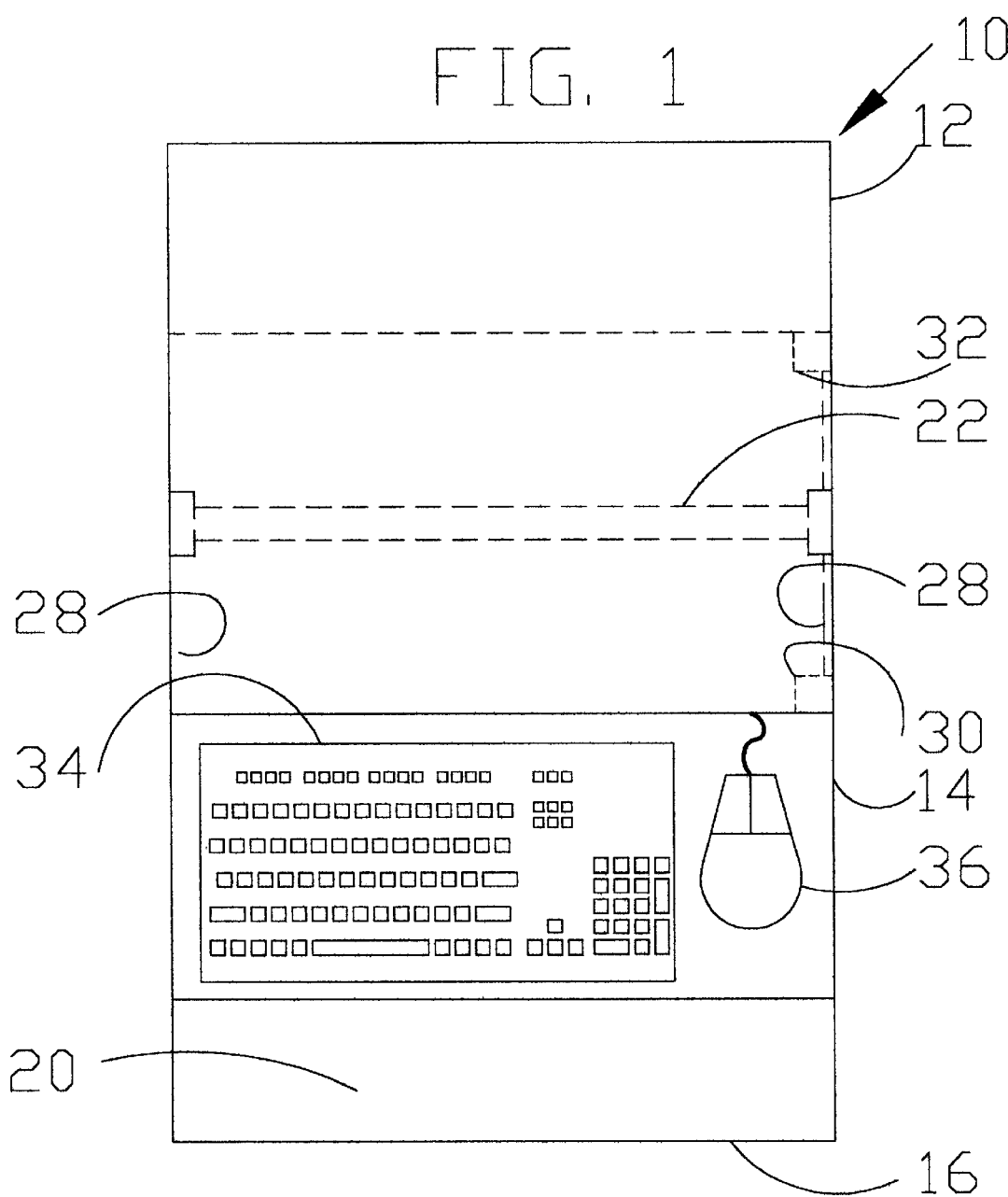
FIG. 1 is a top view of the present invention.
Figure 2:
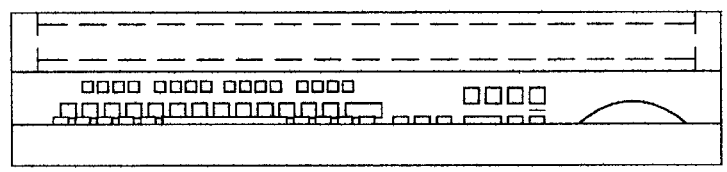
FIG. 2 is a front view of the present invention.
Figure 3:
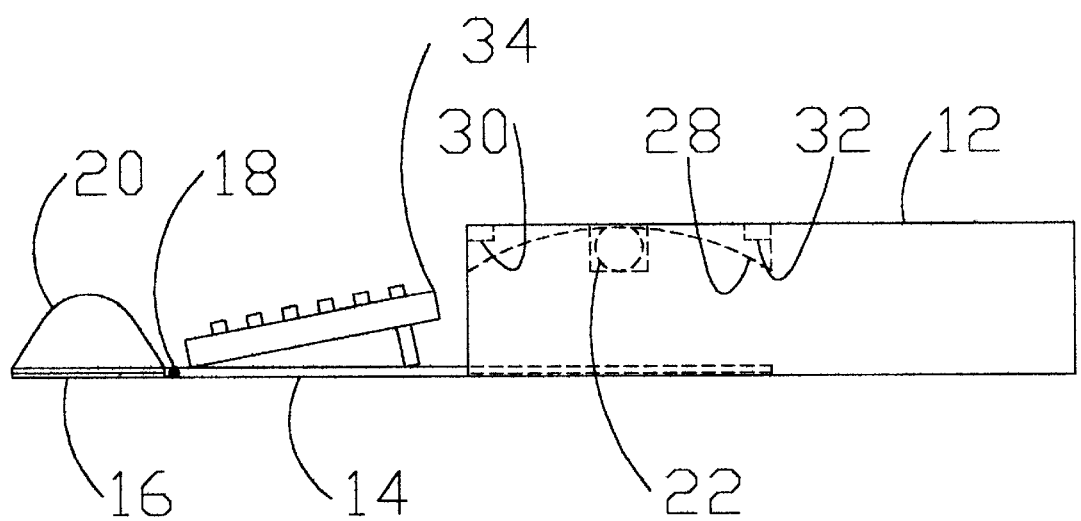
FIG. 3 is an end view of the present invention.

Referring to FIGS. 1, 2 and 3, the reference numeral 10 generally designates the keyboard and mouse sterilizing system embodying the features of the present invention. An enclosure 12 has attached to it a retractable base 14. Various hinge and spring and slidable rails mechanisms are available to store the keyboard ## in the enclosure 12 of the invention 10, and then move the keyboard 34 and mouse 36 to a position for use. A front door 16 is attached to base 14 by a hinge connection 18. A pad 20 is attached to the inside of front door 16. An ultraviolet light 22 is mounted inside of enclosure 12. A switch connection means 24 (not shown) electrically connects ultraviolet light 22 to a power source 26 (not shown). In the preferred embodiment, enclosure 12 is lined with a highly reflective material 28. A safety interlock switch 30 is electrically connected between power source 26 and ultraviolet light 22. A timer module 32 is located inside of enclosure 12 and electrically connected between ultraviolet light 22 and safety interlock switch 30.

Operation of the Invention

Base 14 provides a support surface of a keyboard 34 and a mouse 36 In an extended position, base 14 provides for access to keyboard 34 and mouse 36 by a computer operator. Pad 20 attached to the inside of front door 16 provides a comfortable arm or wrist support for the computer operator. Safety interlock switch 30 prevents operation of ultraviolet light 22 unless and until base 14 is in the retracted position and front door 16 is closed. This can be accomplished by mounting safety interlock switch 30 to the inside of enclosure 12 near to the opening of front door 16. When safety interlock switch 30 is closed, timer module 32 is actuated, initiating a timed duration of operation of ultraviolet light 22. The duration of the ultraviolet light 22 operation is determined by the time required for sterilization While this invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

I claim:

1. A keyboard and mouse sterilizing system comprising:
   an enclosure;
   a retractable base, located in extendable relation to the enclosure;
   a front door, a front door hinge connected to the base;

an ultraviolet light source, located inside on the enclosure;

a switch connection means for controllable connection of the ultraviolet light source to a power source, and a pad attached to the inside of the front door, for arm support of an operator.

2. A keyboard and mouse sterilizing system according to claim 1, the switch connection means further comprising:

a safety interlock switch electrically connected between the ultraviolet light source and a power source, the safety interlock switch actuated by closure of the front door when the base is in the retracted position.

3. A keyboard and mouse sterilizing system according to claim 1, further comprising:

a timer electrically connected between the switch connection means and the ultraviolet light source for controlling the duration of operation of the ultraviolet light source.

* * * * *